United States Patent
Dzhons

(10) Patent No.: US 12,329,878 B2
(45) Date of Patent: Jun. 17, 2025

(54) MATERIAL FOR THE MANUFACTURING OF OPHTHALMIC IMPLANTS BY PHOTO-POLYMERIZATION METHOD

(71) Applicant: LIMITED LIABILITY COMPANY ENTERPRISE "REPER-NN", Nizhny Novgorod (RU)

(72) Inventor: Mihail Mihaylovich Dzhons, Nizhny Novgorod (RU)

(73) Assignee: LIMITED LIABILITY COMPANY ENTERPRISE "REPER-NN", Nizhny Novgorod (RU)

( * ) Notice: Subject to any disclaimer, the term of this patent is extended or adjusted under 35 U.S.C. 154(b) by 521 days.

(21) Appl. No.: 17/757,161

(22) PCT Filed: Dec. 30, 2019

(86) PCT No.: PCT/RU2019/001046
§ 371 (c)(1),
(2) Date: Jun. 10, 2022

(87) PCT Pub. No.: WO2021/137714
PCT Pub. Date: Jul. 8, 2021

(65) Prior Publication Data
US 2023/0054555 A1    Feb. 23, 2023

(51) Int. Cl.
*A61L 27/18* (2006.01)
*C08L 75/16* (2006.01)
*G02B 1/04* (2006.01)

(52) U.S. Cl.
CPC .............. *A61L 27/18* (2013.01); *C08L 75/16* (2013.01); *G02B 1/041* (2013.01)

(58) Field of Classification Search
CPC ......... A61L 27/18; A61F 9/007; A61K 47/16; A61K 47/30; A61P 27/02
USPC ...................................................... 424/427
See application file for complete search history.

(56) References Cited

U.S. PATENT DOCUMENTS

| 4,166,088 A | 8/1979 | Neefe |
| 4,382,902 A | 5/1983 | Feurer |

FOREIGN PATENT DOCUMENTS

| EP | 3323387 B1 | 10/2019 |
| RU | 2074673 C1 | 3/1997 |

OTHER PUBLICATIONS

Molodnyakov S.R. et.al. Polymeric waveguides based on photopolymerizing methacrylate compositions. Russian Journal of Applied Chemistry, 2014, 87(e), pp. 331—doi: 10.1134/s 1070427214030148.
International Search Report for PCT/RU2019/001046; dated Sep. 10, 2020.

*Primary Examiner* — Walter E Webb
(74) *Attorney, Agent, or Firm* — Raven Patents, LLC; Anton E. Skaugset

(57) ABSTRACT

Composite materials, specifically to materials used in medicine, in particular, in ophthalmology for the manufacturing of optical ophthalmic implants, mainly intraocular lenses (IOL), intended for vision correction after cataract removal. The polymerization rate of the material is controlled in order to eliminate defects in the ophthalmic implant profile, control the geometric dimensions, reduce the finished product glistening while keeping optimal physical and mechanical properties. The material for the manufacturing of ophthalmic implants by photo-polymerization method includes:
a) 60-70 wt. % oligomer of urethanedi(meth)acrylate with terminal (meth)acrylate fragments;
b) 20-40 wt. % of (meth)acrylate monomers with aromatic substituents in the side chain;
c) 5-25 wt. % of (meth)acrylate monomers with aliphatic branched substituents in the side chain;
d) at least 0.2 wt. % of a UV-absorbing component;
e) 0.1 to 1 wt. % of photopolymerization initiator; and
f) 0.005 to 0.5 wt. % of a radical polymerization inhibitor.

8 Claims, 1 Drawing Sheet

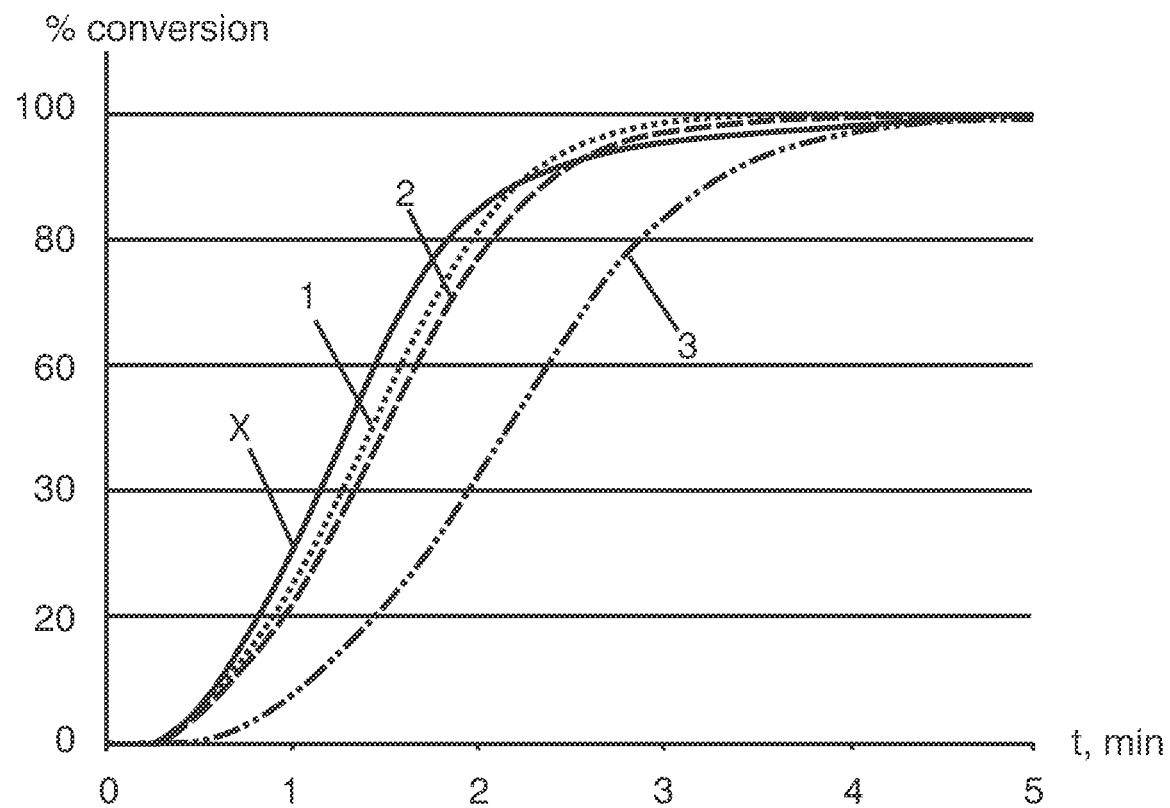

MATERIAL FOR THE MANUFACTURING OF OPHTHALMIC IMPLANTS BY PHOTO-POLYMERIZATION METHOD

TECHNICAL FIELD

The present disclosure relates to the field of composite materials, specifically to materials used in medicine, in particular, in ophthalmology for the manufacturing of optical ophthalmic implants, mainly intraocular lenses (IOL), intended for vision correction after cataract removal.

BACKGROUND

A challenge in modern cataract surgery is to create new IOLs that provide high visual functions to the patient and do not cause complications in the postoperative period. Most of the research is aimed at developing hydrophobic IOLs, which, in comparison with hydrophilic lenses, have a number of advantages: they are more resistant to biodegradation, less likely to cause turbidity of the posterior capsule in the postoperative period (secondary cataract), do not form vacuoles or glare, and are easier to implant due to the use of a pre-installation system. The pre-installation system for hydrophobic IOLs consists in that the IOL is twisted using a special tool, which allows it to be implanted through a small incision. In the eye, the IOL straightens itself and takes the correct position.

As a rule, the IOL has a one-piece structure and consists of an optical part and haptic elements. Haptic elements allow the IOL to adapt to the size of the capsule sack and are compressed in the lens plane.

A material for manufacturing implants disclosed in patent EP3323387B1 is known in the prior art (published on 02.10.2019, A61F2/16, C08G18/67, C08L75/16, C08G18/48, C08G18/76). The disclosed material is a composition for the manufacturing of ophthalmic implants by photopolymerization, which consists of:

a) 35-70 wt. % oligomer of urethanedi(meth)acrylate with terminal (meth)acrylate fragments, which consists of the following components: (I) (meth)acrylate, (II) diisocyanate, and (III) polyol, and has the following structure:

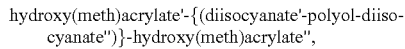

hydroxy(meth)acrylate'-{(diisocyanate'-polyol-diisocyanate")}-hydroxy(meth)acrylate", where one of the isocyanate groups of diisocyanate' and diisocyanate", respectively, is connected to hydroxy(meth)acrylate' and hydroxy(meth)acrylate' to form a urethane bond, and where the remaining isocyanate group of diisocyanate' and diisocyanate", respectively, is connected to the hydroxyl group of polyol to form a urethane bond, where hydroxy(meth)acrylate' and hydroxy(meth)acrylate" may be the same or different, and diisocyanate' and diisocyanate" may be the same or different. Polyol in the oligomer of urethanedi(meth)acrylate can be any aliphatic diol with a branched chain, or be a mixture of several ones.

b) 30-65 wt. % of the component from the group of (meth)acrylate monomers such as: alkyl(meth)acrylates, aryl(meth)acrylates, alicyclic (meth)acrylates, fluorine-substituted (meth)acrylates, silicon-containing (meth)acrylates, any aromatic or aliphatic esters of unsaturated carboxylic acids of not (meth)acrylic series, as well as a mixture of these monomers, where the content of (meth)acrylate monomers with aromatic fragments is at least 50 wt. % of the content of the component b)

c) at least 0.2 wt. % of a UV-absorbing component, such as a polymerizable UV filter including UV-absorbing compounds of the benzophenone or benzotriazole series, or a combination thereof, d) polymerization initiator.

At the same time, the specified material based on a biocompatible copolymer used for the production of hydrophobic ophthalmic implants is hydrophobic with an equilibrium water content of less than 3.0 wt. % at 37° C., while the content of (meth)acrylic acid in the composition of the specified biocompatible copolymer is less than 3 wt. %.

Manufacturing of ophthalmic implants according to the known patent is as follows. A finished product with a given shape and size is obtained by curing a known material under the influence of light between glass injection molds. This method guarantees optical purity, biocompatibility and biostability of the finished product. The known material allows for obtaining high-quality products only when using glass injection molds, which have a transparent pattern of the finished product applied against a material opaque to light (photomask). This production method, for example, is described in patent RU22349391C2 "A method for manufacturing of artificial eye lenses" (published on 20.08.2004, B29D11/00, A61F2/16). For the manufacturing of artificial lenses of the eye, this method uses an injection mold consisting of two halves made of an optically transparent material, such as quartz, and an annular gasket, the thickness of which is equal to the thickness of the supporting part of the lens. The inner surface of the upper half of the mold has a pattern containing UV light transparent and opaque areas, for example, made of chromium, the negative image of which corresponds to a flat image of the optical part of the lens and its supporting elements. The inner surface of the second half of the mold has a similar pattern, the negative image of which corresponds only to the optical part of the lens.

In this case, polymerization in opaque (dark) areas is almost impossible as no light can enter them. When carrying out the process of obtaining a finished product without using any patterns or coatings on glass injection molds, based on the principle of projection rather than contact lithography, the disadvantage of the material disclosed in EP3323387B1 is the lack of the polymerization rate control (inhibition for a significant time) in dark (unlit) areas, which results in:

possible defects on the end face along the IOL edge, i.e. microirregularities perceived as an untreated edge. It is also possible that the geometric dimensions of the haptic elements significantly change (widen), which directly affects the physical and mechanical properties so that he haptic elements would not compress properly during implantation, and the IOL may also be improperly positioned in the capsule sack after implantation, if there are orifices in the IOL structure, those orifices could bloat and, as a result, not fulfill their intended function when the IOL is being positioned.

The lack of polymerization rate control in the known material also complicates the possibility of obtaining a more uniform structure with less free volume and increases the likelihood of glistening.

SUMMARY

The technical result is to control the polymerization rate in order to eliminate defects in the ophthalmic implant profile, control the geometric dimensions, reduce the finished product glistening while keeping optimal physical and mechanical properties.

The technical result is achieved by means of a material proposed for the manufacturing of ophthalmic implants by photopolymerization, comprising:
a) 60-70 wt. % oligomer of urethanedi(meth)acrylate with terminal (meth)acrylate fragments;
b) 20-40 wt. % of (meth)acrylate monomers with aromatic substituents in the side chain;
c) 5-25 wt. % of (meth)acrylate monomers with aliphatic branched substituents in the side chain;
d) at least 0.2 wt. % of a UV-absorbing component;
e) 0.1 to 1 wt. % of photopolymerization initiator; and
f) 0.005 to 0.5 wt. % of a radical polymerization inhibitor.

BRIEF DESCRIPTION OF THE DRAWING

FIG. 1. shows the kinetic evaluation results for the photopolymerization of the cured compositions of the test samples according to Table 1 when irradiated with a LED source with a wavelength of 405-410 nm and a power of 1-2 mW/cm$^2$.

DETAILED DESCRIPTION

The material of the present disclosure for the manufacturing of ophthalmic implants by photopolymerization includes:
a) 60-70 wt. % oligomer of urethanedi(meth)acrylate with terminal (meth)acrylate fragments, which consists of the following components: (I) (meth)acrylate, (II) diisocyanate, and (III) polyol, and has the following structure:

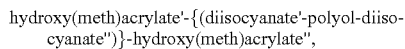

where one of the isocyanate groups of diisocyanate' and diisocyanate", respectively, is connected to hydroxy(meth)acrylate' and hydroxy(meth)acrylate' to form a urethane bond, and where the remaining isocyanate group of diisocyanate' and diisocyanate", respectively, is connected to the hydroxyl group of polyol to form a urethane bond, where hydroxy(meth)acrylate' and hydroxy(meth)acrylate" may be the same or different, and diisocyanate' and diisocyanate" may be the same or different, and polyol in the oligomer of urethanedi(meth)acrylate can be any aliphatic diol with a branched chain, or be a mixture of several ones,
b) 20-40 wt. % of the component from the group of (meth)acrylate monomers with aromatic substituents in the side chain, and include at least one of the following: 2-phenoxyethylmethacrylate, benzylmethacrylate, benzyl-2-ethylacrylate, phenylmethacrylate,
c) 5-25 wt. % of the component from the group of (meth)acrylate monomers with aliphatic branched substituents in the side chain, and includes at least one of the following: tert-butylmethacrylate, isobutylmethacrylate, 2-ethylhexylmethacrylate,
d) at least 0.2 wt. % of a UV-absorbing component, such as a polymerizable UV filter including UV-absorbing compounds of the benzophenone or benzotriazole series, or a combination thereof,
e) 0.1 to 1 wt. % of photopolymerization initiator,
f) 0.005 to 0.5 wt. % of a radical polymerization inhibitor, and includes at least one of the following: 4-tert-butylpyrocatechol; tert-butylhydroquinone; 1,4-benzoquinone; 6-tert-butyl-2,4-xylenol; 2-tert-butyl-1,4-benzoquinone; 3,5-di-tert-butyl-o-benzoquinone; 2,6-di-tert-butyl-p-cresol; 2,6-di-tert-butylphenol; hydroquinone; 4-methoxyphenol.

Photopolymerization initiator, component e), preferably selected from the following: IRGACURE 369: 2-benzyl-2-(dimethylamino)-1-[4-(4-morpholinil)phenyl]-1-butanone; IRGACURE 651: 2,2-dimethoxy-2-phenyl acetophenone; DAROCUR TPO: 2,4,6-trimethylbenzoyl-diphenyl-phosphinoxide; DAROCUR 4265: mixture of DAROCUR TPO and DAROCUR 1173: 2-hydroxy-2-methyl-1-phenyl-1-propanone; IRGACURE 2100: mixture of ethyl ether 2,4,6-trimethylbenzoyl-phenylphosphic acid and IRGACURE 819: phenylbis(2,4,6-trimethylbenzoyl)phosphinoxide; IRGACURE 2022: mixture of IRGACURE 819 and DAROCUR 1173; IRGACURE 2022: mixture of bis(2,6-dimethoxybenzoyl-2,4,4-trimethylpentyl)phosphinoxide and 2-hydroxy-2-methyl-1-phenyl-propane-1-one.

As a UV-blocking component, component d), the material may contain diphenyl ketone-type compounds, such as 2-hydroxy-4-acryloyloxydiphenyl ketone, 2-(4-benzoyl-3-hydroxyphenoxy)ethylacrylate, and polymerizable benzotriazole-type UV filters, such as 2-[3-(2H-benzotriazole-2-yl)-4-hydroxyphenyl]ethylmethacrylate, 2-[2-hydroxy-5-[2-(methacryloyloxy)ethyl]phenyl]-2H-benzotriazole. A combination of these components can also be used.

The material may additionally contain a component that absorbs the blue part of the spectrum.

The material for the manufacturing of ophthalmic implants according to the present disclosure is polymerized by light curing (by photopolymerization) in transparent injection molds without additional coatings. The method for obtaining the finished product by photopolymerization consists in irradiating the material with light that has previously passed through the corresponding photomask and has the appropriate wavelength, for example, 340 Nm to 450 Nm, preferably, 360 Nm to 430 Nm, more preferably about 410 Nm. The irradiation time can be 1 to 7 minutes, preferably about 3 minutes. In particular, the photopolymerization method can be applied at 410 Nm for 1-5 minutes, preferably for 3 minutes. The light source used should preferably have a power of 1-5 mW/cm$^2$.

An Embodiment of the Present Disclosure

The material of the present disclosure can be illustrated by the following examples.

EXAMPLE 1

Test samples of material for the manufacturing of ophthalmic implants by photopolymerization with varying composition of components presented in Table 1 were prepared as follows. Samples of finished IOLs (+20 dptr) were obtained by curing between two corresponding glass injection molds using a LED source with a wavelength of 405-410 nm and a power of 1-2 mW/cm$^2$, then the finished lenses, after washing off the remnants of the unpolymerized composition, were additionally illuminated in a vacuum chamber using the same light source for 30 minutes. The cured samples were extracted with isopropyl alcohol at 60-70° C. for 5 hours, and then dried in vacuum for 12 hours at 60° C.

TABLE 1

| Sample No. | Composition contents | | | | | | | Properties | |
|---|---|---|---|---|---|---|---|---|---|
| | OUA, wt. % | BenzMA, wt. % | TMBA, wt. % | n-OMA, wt. % | UV filter, wt. % | Photo-initiator, wt. % | DTBPC inhibitor, wt. % | Polymerization rate, %/min | The offset of dimensions towards the dark area, the illumination time is 2 minutes | The curing time without the offset of dimension, min |
| X | 62 | 25 | — | 10 | 2 | 0.25 | — | 64 | yes | 1.5 |
| 1 | 62 | 25 | 10 | — | 2 | 0.25 | 0.01 | 62 | no | 2.0 |
| 2 | 62 | 25 | 10 | — | 2 | 0.25 | 0.04 | 59 | no | 2.5 |
| 3 | 62 | 25 | 10 | — | 2 | 0.25 | 0.1 | 46 | no | 3.2 | where
test sample X corresponds to the closest analog for the proposed material for the manufacturing of ophthalmic implants disclosed in EP3323387B1, published on 02.10.2019, A61F2/16, C08G18/67, C08L75/16, C08G18/48, C08G18/76.
test samples 1-3 correspond to the proposed material for the manufacturing of ophthalmic implants, but do not limit it.
OUA—oligomer of urethanedi(meth)acrylate with the structure:

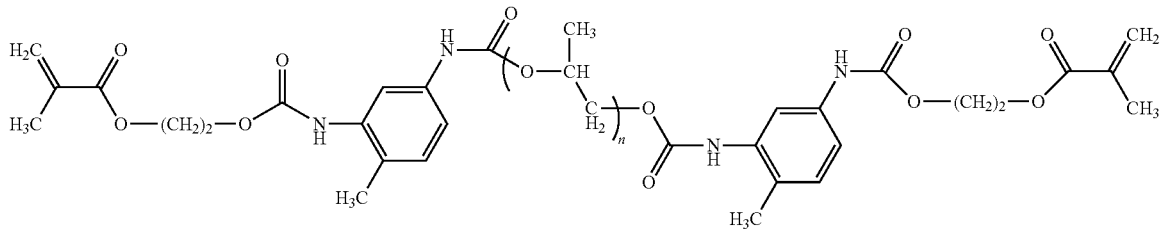

BenzMA—benzyl methacrylate,
n-OMA—n-octyl methacrylate,
TBMA—tert-butyl methacrylate,
UV filter—2-[3(2H-benzotriazole-2-yl)-4-hydroxyphenyl] ethylmethacrylate
Photoinitiator—IRGTPO—2,4,6-trimethylbenzoyl diphenylphosphinoxide
DTBPC—2,6-di-tert-butyl-p-cresol According to FIG. 1, the addition of a radical polymerization inhibitor reduces the polymerization rate, especially when large amounts of it are present. In this case, the polymerization rate in the dark area will decrease even more due to the low power of light entering this area due to scattering and reflection. Thus, as follows from FIG. 1 and from Table 1, it is most preferable to use moderate amounts of the inhibitor, about 0.05 wt. %, since it is the case when the greatest difference is observed between the time of complete curing (time t on FIG. 1) in the irradiated area and the maximum illumination time, at which no polymerization results are observed in the dark area.

The test showed that the effect of glistening in test samples 1-3 is much less pronounced than in sample X.

The invention claimed is:
1. A material for manufacture of ophthalmic implants by photo-polymerization, comprising:

a) 60-70 wt. % of an oligomer of urethanedi(meth)acrylate having terminal (meth)acrylate fragments, the oligomer of urethanedi(meth)acrylate having components (I) (meth)acrylate, (II) diisocyanate, and (III) polyol, according to the following structural formula:

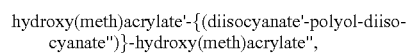

where one of the isocyanate groups of diisocyanate' and diisocyanate", respectively, is connected to hydroxy (meth)acrylate' and hydroxy(meth)acrylate' to form a urethane bond, and where the remaining isocyanate group of diisocyanate' and diisocyanate", respectively, is connected to the hydroxyl group of polyol to form a urethane bond, where hydroxy(meth)acrylate' and hydroxy(meth)acrylate" may be the same or different, and diisocyanate' and diisocyanate" may be the same or different, and polyol in the oligomer of urethanedi (meth)acrylate can be any aliphatic diol with a branched chain, or a mixture of aliphatic diols with branched chains, b) 20-40 wt. % of components from a group of (meth) acrylate monomers with aromatic substituents in a side chain, including at least one of 2-phenoxyethylmethacrylate, benzylmethacrylate, benzyl-2-ethylacrylate, and phenylmethacrylate, c) 5-25 wt. % of components from a group of (meth) acrylate monomers with aliphatic branched substituents in a side chain, including at least one of tert-butylmethacrylate, isobutylmethacrylate, and 2-ethylhexylmethacrylate, d) at least 0.2 wt. % of one or more UV-absorbing components, e) 0.1 to 1 wt. % of a photopolymerization initiator, f) 0.005 to 0.5 wt. % of a radical polymerization inhibitor, including at least one of 4-tert-butylpyrocatechol; tert-butylhydroquinone; 1,4-benzoquinone; 6-tert-butyl-2,4-xylenol; 2-tert-butyl-1,4-benzoquinone; 3,5-di-tert-butyl-o-benzoquinone; 2,6-di-tert-butyl-p-cresol; 2,6-di-tert-butylphenol; hydroquinone; and 4-methoxyphenol.

2. The material according to claim 1, wherein the oligomer of urethanedi(meth)acrylate having terminal (meth)acrylate fragments has the structure:

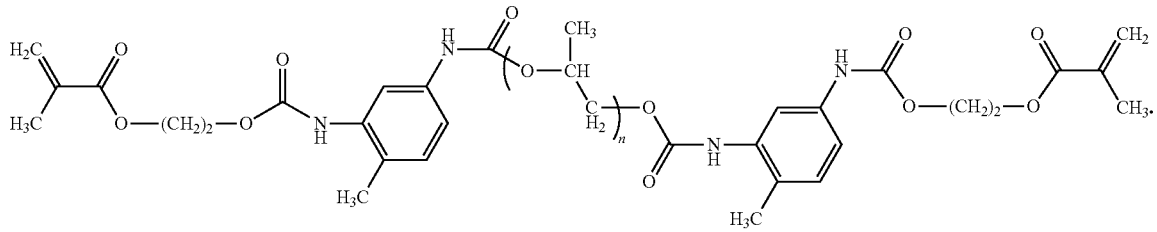

3. The material according to claim 1, wherein the components from the group of (meth)acrylate monomers with aromatic substituents in the side chain includes benzyl methacrylate.

4. The material according to claim 1, wherein the components from the group of (meth)acrylate monomers with aliphatic branched substituents in the side chain, includes tert-butyl methacrylate.

5. The material according to claim 1, wherein the at least 0.2 wt. % of one or more UV-absorbing components includes a polymerizable UV filter.

6. The material according to claim 5, wherein the polymerizable UV filter includes one or more UV-absorbing compounds of a benzophenone or a benzotriazole series.

7. The material according to claim 1, wherein the photopolymerization initiator includes 2,4,6-trimethylbenzoyl diphenylphosphinoxide.

8. The material according to claim 1, wherein the radical polymerization inhibitor includes 2,6-di-tert-butyl-p-cresol.

* * * * *